United States Patent [19]
Kreuzer et al.

[11] Patent Number: 5,116,323
[45] Date of Patent: May 26, 1992

[54] ARTERIAL CATHETER

[75] Inventors: James A. Kreuzer, Bellbrook; Min S. Lee, Spring Valley, both of Ohio

[73] Assignee: Becton, Dickinson and Company, Franklin Lakes, N.J.

[21] Appl. No.: 644,067

[22] Filed: Jan. 22, 1991

[51] Int. Cl.⁵ .................. A61M 5/178; A61M 25/01
[52] U.S. Cl. ............................. 604/164; 604/280
[58] Field of Search .................. 604/158–170, 604/280, 264, 171; 128/658, 772

[56] References Cited

U.S. PATENT DOCUMENTS

| | | |
|---|---|---|
| 3,572,334 | 3/1971 | Petterson ............................ 604/159 |
| 3,595,230 | 7/1971 | Suyeoka et al. .................... 604/171 |
| 3,727,602 | 4/1973 | Hyden et al. ....................... 604/164 |
| 3,825,001 | 7/1974 | Bennet et al. ...................... 128/214.4 |
| 4,417,886 | 11/1983 | Frankhouser et al. ............. 604/53 |
| 4,772,264 | 9/1988 | Cragg ................................... 604/168 |
| 4,863,431 | 9/1989 | Vaillancourt ....................... 604/168 |
| 4,961,729 | 10/1990 | Vaillancourt ....................... 604/168 |
| 5,019,049 | 5/1991 | Haining .............................. 604/165 |

Primary Examiner—C. Fred Rosenbaum
Assistant Examiner—William Lewis
Attorney, Agent, or Firm—Robert P. Grindle

[57] ABSTRACT

An assembly is provided for easing the insertion and placement of an arterial catheter in the blood vessel of a patient. The assembly includes the combination of an insertion needle and guide tube which pass through the lumen of a catheter, and prior to use extends slightly out of the distal end of the catheter. The needle, in turn, extends slightly out of the distal end of the guide tube and serves to make the initial insertion through the skin and into the blood vessel. Once initial insertion is made, as indicated by blood "flash back" to the transparent needle hub, the guide tube is advanced through the catheter to provide a tracking path for the catheter. Once the distal end of the catheter has followed the guide tube path, the guide tube and needle are withdrawn. A feature of the invention is a guide tube slide arrangement for controlling the advance and retraction of the guide tube.

5 Claims, 1 Drawing Sheet

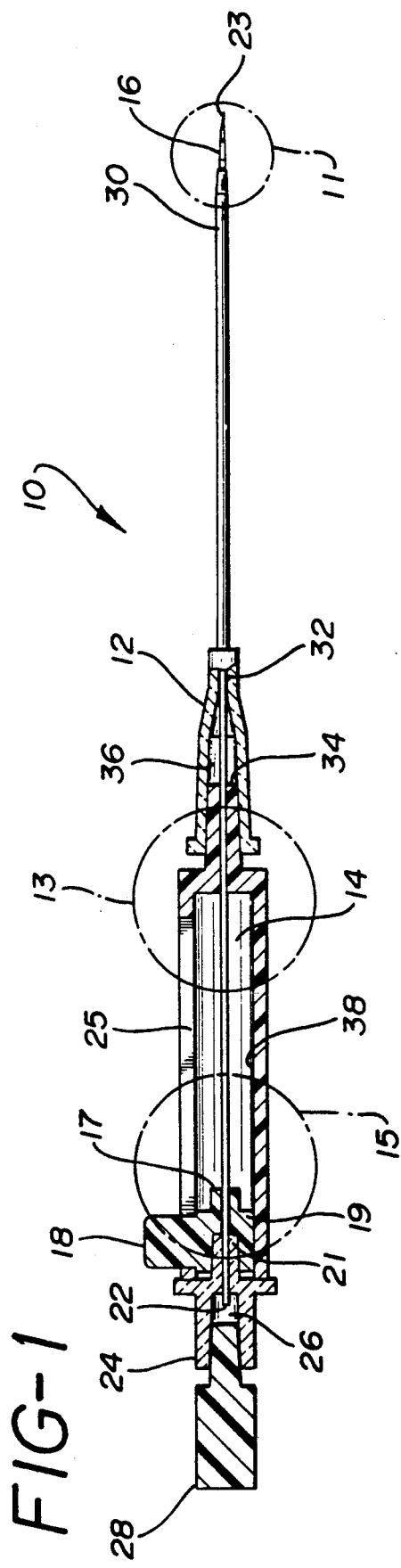
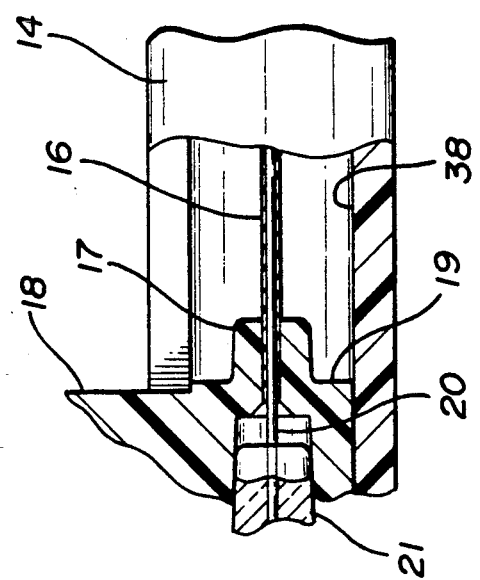
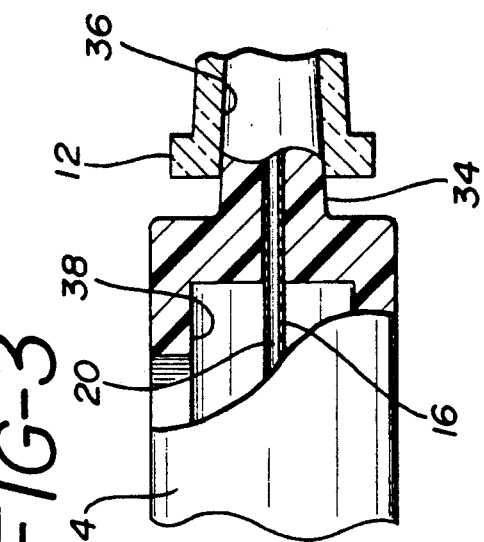
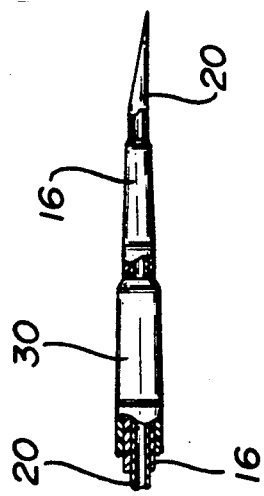

ARTERIAL CATHETER

BACKGROUND AND DESCRIPTION OF THE INVENTION

Generally speaking, this invention relates to an arterial catheter placement assembly. More particularly, this invention relates to such an assembly which provides ease of insertion and placement of the distal end of the catheter in the blood vessel of a patient in the desired location. That is, the assembly includes a combination needle and guide tube, both of which pass through the lumen of the catheter and extend slightly out the front end thereof prior to use. The assembly includes a guide tube slide mounted on the proximal end of the guide tube for controlling the advance and retraction of the guide tube in the assembly of the invention.

In the insertion and placement of a catheter, it is most important to ease as much as possible the movement through the skin of the patient and into the blood vessel. This is important not only from the standpoint of reducing the amount of pain entailed in such a procedure, but also in precise placement of the distal end of the catheter without any undue movement or experimentation.

In the past, placement assemblies of the kind discussed herein have included a guidewire which extends through the needle for providing a "track" for the movement of the catheter into its desired position in the blood vessel of a patient. Representative of such arrangements include, for example, U.S. Pat. No. 4,417,886 which teaches a catheter introduction set utilizing the combination of a needle and guidewire. In such an arrangement, the needle sharpened distal point is utilized to make an introduction through the skin of a patient and into the blood vessel thereof. Thereafter, the guidewire is moved forward through the blood vessel of the patient to the position where the distal end of the resulting catheter is desired. Then, the catheter is moved forward over the guidewire into the desired location. Once this takes place, the guidewire and needle are withdrawn. However, because of the flexibility of the guidewire itself, the actual positioning of the guidewire in the blood vessel may be somewhat tentative, simply because of lack of control of the movement of a wire.

With this invention by contrast, a combination needle and guide tube assembly are provided. That is, the needle and guide tube are positioned coaxially with the catheter and pass through the lumen thereof. The needle, in turn, passes through the lumen of the guide tube. In the initial positioning of the placement device of the invention here, the distal end of the needle extends slightly out of the distal end of the guide tube which in turn extends slightly out of the distal end of the catheter. Positioned on the rear end of the guide tube is a guide tube slide arrangement with a slide handle for manipulating the advancement and retraction of the guide tube.

Thus, the user inserts the needle through the skin of the patient and through the wall of the blood vessel under consideration. Thereafter, blood vessel entry is indicated in the transparent hub of the needle. Then, using the slide arrangement for the guide tube, the operator may advance the guide tube through the desired path in the blood vessel for providing a final path for positioning the distal end of the catheter. Subsequent to this controlled advancement of the guide tube, the catheter is advanced following the path initiated by the guide tube.

After this procedure has taken place, the guide tube and the needle may be withdrawn so that the catheter hub may be connected to appropriate equipment for blood draw, blood transfusion or the delivery of fluids or drugs.

As will be understood by practitioners-in-the-art, the entire circumferential extent of the catheter is guided by the guide tube path for insertion of the catheter to the precise location desired. Control is much more precise than is the case with use of a wire as a guide.

U.S. Pat. No. 3,825,001 teaches a catheter placement arrangement utilizing a guide tube. However, the guide tube assembly is locked in place on the proximal end hub of the catheter. There is no free manipulation of the guide tube to advance it forwardly and to withdraw it. It is simply removed from the hub of the catheter once placement has taken place.

With this invention, by contrast, the guide tube assembly with the slide control arrangement for placing the guide tube and withdrawing it includes a cooperating male luer lock connection which cooperates with the female luer lock connection of the catheter hub for ease of assembly and removal once placement has taken place. Nevertheless, the slide here provides guided advance for precise positioning of the catheter.

Other objects and advantages of this invention will be apparent from the following description, the accompanying drawings and the appended claims.

DESCRIPTION OF THE DRAWINGS

FIG. 1 is a longitudinal sectional view of a catheter placement assembly illustrating the invention;

FIG. 2 is an enlarged perspective view partially in section of a portion of the assembly of FIG. 1 as shown in the area defined by circle 11, and showing the cooperating positioning of the needle, the guide tube and the catheter of the assembly of the invention; and FIG. 3 is an enlarged partially sectional view of a portion of FIG. I, defined by circle 13 and showing the connection in detail of the catheter hub with the guide tube slide body of the invention; and FIG. 4 is an enlarged partially sectional view of a portion of FIG. 1, defined by circle 15 and showing the connection in detail of the guide tube slide body and the needle hub.

DETAILED DESCRIPTION OF THE INVENTION

Referring to the drawings, in which like reference characters refer to like parts throughout the several views thereof, FIG. 1 shows a catheter placement assembly generally designated 10 having a catheter hub 12 with a catheter 30 positioned in the front end opening 32 of catheter hub 12. Catheter hub 12 includes a female luer lock connection 36 tapered in the usual manner to receive the male luer lock connection 34 of a guide tube slide body 14.

The latter has a bore 38 therein for receiving in longitudinal sliding cooperating engagement a guide tube hub or slide body 19 controlled by a guide tube slide handle 18. Guide tube slide body 19 has a slot 25 for receiving handle 18 in sliding engagement. The guide tube slide body 19 includes a distal integral portion 17 for receiving therein a guide tube 16. Guide tube 16 passes through the catheter 30 and extends outwardly from the front end thereof as shown in FIG. 2. Again, guide tube slide body 19 includes, in the proximal end thereof, a cooperating luer lock connection 21 providing cooperating tapered surfaces with the distal end of needle hub 24.

Positioned in an integral forward extension 21 of needle hub 24 is a needle 20, the proximal end 22 of which extends into chamber 26 of the transparent hub 24 for indicating "flash back" once blood has been passed through needle 20 from the point 23 thereof when 23 has passed into the blood vessel of a patient during a placement procedure.

As can be seen in FIGS. 1 and 2, needle 20 extends through tube 16 and catheter 30 to extend outwardly a short distance from the guide tube 16.

The assembly includes a plug 28 for plugging the proximal end of needle hub 24. Plug 28 includes the usual air bleeding arrangement (not shown), as will be understood by practitioners-in-the art, to allow displacement of air from chamber 26 when blood moves rearwardly from point 23 to proximal end 22 of needle 20.

Thus, in use, the assembly has the distal end thereof positioned substantially as shown in FIG. 2. The technician inserts needle point 23 through the skin of a patient and into the blood vessel in question. Once insertion has been made and there has been flash back indication in chamber 26 through the transparent walls of needle hub 24, the slide handle 18 may be grasped by the user to advance the guide tube 16 forwardly over the needle point and into the blood vessel. Then, the guide tube 16 is advanced to the desired location in the blood vessel.

Because the guide tube is passing through the lumen of the catheter and is in the form of a tube, it may be easily controlled to advance to the position desired. Once this has taken place, catheter 30 is advanced forwardly following the track of guide tube 16 into the desired position in the vessel. Guide tube 16 may be advanced through the use of the slide 19 and slide handle 18 to the desired position. Once positioning of the distal end of catheter 30 has taken place, guide tube 16 is withdrawn by use of handle 18 moving slide body 19 rearwardly through guide tube slide body 14.

Thereafter, the needle, hub 24 and plug 20 together with the distal hub 34 of guide tube slide body 14 are withdrawn from the proximal end of catheter hub 12, and appropriate equipment is connected to the placed catheter 30, utilizing the female luer lock connection 36 of hub 12.

As purely illustrative of materials which may be utilized for the guide tube of the invention, polyurethane formulations providing softening of the guide tube body upon exposure to blood is representative. One such formulation is Vialon®, a trademark of Becton, Dickinson and Company, designating a specific polyurethane formulation for that purpose. Of course, the same materials may be utilized for the catheter itself.

Thus, as will be appreciated from the above, there is provided in accordance with this invention a placement assembly for arterial catheters which provides a much more precise placement of the distal end of the catheter in the blood vessel of a patient. The slide arrangement provides much more precise control in advancement and withdrawal of the guide tube. Moreover, the fact that the guiding arrangement, in accordance herewith, is in fact, a tube, the entire circumferential extent of the catheter wall is appropriately guided during the entire guiding path provided by the guide tube of the invention.

While the forms of apparatus herein described constitute preferred embodiments of the invention, it is to be understood that the invention is not limited to these precise forms of apparatus, and that changes may be made therein without departing from the scope of the invention which is defined in the appended claims.

What is claimed is:

1. A catheter placement assembly, comprising
   (a) a catheter having a distal end, a proximal end, and a lumen extending from said distal end to said proximal end;
   (b) a catheter hub positioned on the proximal end of said catheter;
   (c) a catheter placement tube extending coaxially through said catheter lumen;
   (d) said catheter placement tube having a distal end, a proximal end and a lumen extending from said distal end to said proximal end;
   (e) a catheter tube slide body positioned on said catheter placement tube adjacent the said proximal end of said catheter placement tube;
   (f) a catheter tube slide positioned on said proximal end of said catheter placement tube;
   (g) said catheter tube slide mounted for relative reciprocable movement in said catheter tube slide body;
   (h) a catheter placement tube hub positioned on said distal end of said catheter tube slide body for detachable connection to said catheter hub;
   (i) an insertion needle extending coaxially through said catheter placement tube lumen;
   (j) said insertion needle having a sharpened distal end extending outwardly from said distal end of said catheter placement tube, and a lumen extending from said distal end to the proximal end thereof;
   (k) a transparent hollow needle hub positioned on said proximal end of said insertion needle for detachable connection to said catheter tube slide; and
   (l) means in said transparent needle hub for venting air therefrom when the said distal end of said needle makes vein entry;
   (m) whereby when vein entry has been made, said needle hub is removed from said catheter tube slide body, said needle is removed from said catheter placement tube lumen and said catheter tube slide is moved forward distally through said catheter lumen to provide a guide path for said catheter distal end.

2. The catheter placement assembly of claim 1, wherein
   (a) said detachable connection between said catheter tube slide body and said catheter hub is a luer lock connection.

3. The catheter placement assembly of claim 1, wherein
   (a) said detachable connection between said needle hub and catheter hub slide is a luer lock connection.

4. The catheter placement assembly of claim 1, wherein
   (a) said catheter tube slide body has an elongated slot;
   (b) a handle on said catheter tube slide;
   (c) said handle extending through said slot for moving said catheter tube slide along said catheter tube slide body.

5. The catheter placement assembly of claim 1, wherein
   (a) said catheter and said catheter placement tube are comprised of a material which softens when exposed to blood.

* * * * *